(12) United States Patent
Xie et al.

(10) Patent No.: US 10,058,636 B2
(45) Date of Patent: Aug. 28, 2018

(54) DRUG COATED BALLOON CATHETER

(71) Applicant: Lifetech Scientific (Shenzhen) Co., Ltd., Shenzhen (CN)

(72) Inventors: Qizong Xie, Shenzhen (CN); Yongmu Zhang, Shenzhen (CN); Jinhua Lu, Shenzhen (CN); Jingzhong Song, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 116 days.

(21) Appl. No.: 15/107,806

(22) PCT Filed: Dec. 8, 2014

(86) PCT No.: PCT/CN2014/093305
§ 371 (c)(1),
(2) Date: Jun. 23, 2016

(87) PCT Pub. No.: WO2015/096614
PCT Pub. Date: Jul. 2, 2015

(65) Prior Publication Data
US 2016/0331870 A1    Nov. 17, 2016

(30) Foreign Application Priority Data
Dec. 26, 2013  (CN) .......................... 2013 1 0732989

(51) Int. Cl.
*A61L 29/16* (2006.01)
*A61L 29/06* (2006.01)
(Continued)

(52) U.S. Cl.
CPC .............. *A61L 29/16* (2013.01); *A61L 29/06* (2013.01); *A61L 29/14* (2013.01); *A61M 25/10* (2013.01);
(Continued)

(58) Field of Classification Search
CPC .......... A61L 29/16; A61L 29/08; A61M 25/10
See application file for complete search history.

(56) References Cited

U.S. PATENT DOCUMENTS 5,071,429 A * 12/1991 Pinchuk ............ A61M 25/1025
600/116
2008/0118544 A1 * 5/2008 Wang ................... A61K 31/337
424/423

OTHER PUBLICATIONS

International Search Report dated Mar. 11, 2015 for PCT/CN2014/093305.

* cited by examiner

*Primary Examiner* — Laura Bouchelle
*Assistant Examiner* — Tasnim M Ahmed
(74) *Attorney, Agent, or Firm* — Raymond Sun

(57) ABSTRACT

A drug coated balloon catheter has a balloon and a drug coating covering the surface of the balloon; the drug coating comprises an active drug and a carrier; the active drug is paclitaxel, rapamycin, a paclitaxel derivative or rapamycin derivative; the carrier comprises an organic acid salt and polyalcohol; a mass ratio of the active drug to the carrier in the drug coating is 0.2 to 100, and a mass ratio of the organic acid salt to the polyalcohol is (0.2 to 5):1. The organic acid salt and the polyalcohol in the drug coating jointly take effect to prevent the premature release of drugs before the balloon catheter is positioned at a target site, and to promote the drugs being quickly released from the surface of the balloon and absorbed by the target tissue, thus reducing drug loss during transmission, and also having a better drug transfer effect.

12 Claims, 1 Drawing Sheet

(51) Int. Cl.
*A61L 29/14* (2006.01)
*A61M 25/10* (2013.01)
(52) U.S. Cl.
CPC .. *A61L 2300/416* (2013.01); *A61M 2025/105* (2013.01)

DRUG COATED BALLOON CATHETER

TECHNICAL FIELD

The present invention relates to interventional medical instruments, and in particular, to a drug coated balloon catheter.

BACKGROUND OF THE PRESENT INVENTION

The field of cardiovascular interventional therapy has experienced three milestone leaps from the 70's in last century to now. In 1977, a balloon was used for the first time to dilate coronary artery stenosis in a human, as the first milestone. Although the balloon dilation could eliminate the coronary artery stenosis, due to the elasticity recoil of the vascular wall, intimal hyperplasia and vascular wall intimal tear and the like, vascular restenosis may re-occur again, and the restenosis rate of the target vessel reaches up to 30 to 50% after post-operative 3 to 6 months. The advent of a bare metal stent in 1986, is the second milestone of the interventional therapy, which could not only eliminate the short-term vascular stenosis, but could also greatly reduce the acute occlusion rate. However, the restenosis rate of the target vessel can still reach up to 30%. A drug eluting stent came out in 2001, as the third milestone, to reduce the restenosis rate of the target vessel to below 3%.

The stent may treat the atherosclerosis and the vascular stenosis, but the risk of restenosis will still exist in the blood vessel and the stent, and the therapeutic effect of the stent on small vessels, bifurcation vessels, in situ lesions and the like is not ideal. At present, the method for treating restenosis includes re-dilatation using a conventional balloon, oriented atherectomy, rotational atherectomy, endovascular radiotherapy, repeated stenting, and so on. The existing uncoated balloons and drug eluting stents all have certain limitations. The restenosis rate of the uncoated balloon is higher, and the therapeutic effect of the drug eluting stent on small vessels and bifurcation vessels is poor; both of the uncoated balloon and the drug eluting stent fail to show sufficient effectiveness or safety thereof.

The advent of a drug eluting balloon has brought a new hope to treat restenosis. The prior drug coated balloon treats the coronary artery restenosis by applying a drug coating on the balloon catheter, with a contrast agent iopromide as a carrier together with paclitaxel regarded as the drug coating, which may improve the drug transfer rate. However, the contrast agent in the diagnostic process can provide a certain incidence of complications. Moreover, as a large hydrophilic molecule, the iopromide might not effectively carry the lipophilic paclitaxel to penetrate through the membrane lipid bilayer into the cell.

The key technical point of the drug coated balloon is how to achieve a bond balance between the drug coating and the surface of the balloon. If the adhesive force between the drug coating and the surface of the balloon is smaller, the drug can easily fall off during the folding of the balloon, or be lost during the delivery process for placing at a lesion site, or could burst and fall off in the expansion process before coming in contact with the target tissue, and then flushed away by the high speed flowed blood. If the adhesive force between the drug coating and the surface of the balloon is too large, the drug cannot be easily transferred to the tissue when the balloon contacts the target lesion tissue.

SUMMARY OF THE PRESENT INVENTION

To address the deficiencies of the prior art, a highly targeted coating for medical instruments is required to be developed, which may quickly and directly deliver an active drug to a local tissue region during or after the clinical procedure. The balloon catheter should quickly release the active drug at a required target position effectively and efficiently, so that the active drug may quickly penetrate into the target tissue for treating the applicable diseases; e.g., for relieving the vascular lumen stenosis and preventing body lumen restenosis or late lumen loss.

An object of the present invention is to provide a balloon catheter with a rapid drug release coating, which is configured to deliver the active drug to the target sites of the vessels or lumens. The drug coating is applied to the outer surface of the balloon catheter, and the drug coating contains active drug/drugs and carrier/carriers. The carrier accelerates the release rate of the active drug from the balloon. The drug is released in a very short period of time and quickly penetrates into the tissue of the diseased site, so as to improve the absorption ratio of the drug in the diseased tissue of the vascular system or other body lumens, and to reduce the drug loss in the clinical use and delivery process, and to promote quick transfer of the drug to the target lesion site after dilatation of the balloon.

In order to achieve the objective, the present invention adopts a technical solution as follows.

A drug coated balloon catheter is provided, comprising a balloon and a drug coating on the outer surface of the balloon; the drug coating includes active drug/drugs and carrier/carriers; the active drug is paclitaxel, rapamycin, paclitaxel derivatives or rapamycin derivatives; the carriers includes organic acid salt and polyalcohol; a mass ratio of the active drug to the carriers in the drug coating is 0.2 to 100, and a mass ratio of the organic acid salt to the polyalcohol is (0.2 to 5):1.

The organic acid salt is one or more than two of acetate, benzoate, maleate, succinate, ascorbate, citrate, tartrate, lactate, oxalate, aspartate, nicotinate, gluconate, glutamate, vanillate and lactobionate; the polyalcohol is one or more than two of polyethylene glycol, trometamol, xylitol, sorbitol, mannitol, amino alcohol.

The content of the active drug on the outer surface of the balloon is 0.5 to 20 μg/mm$^2$.

The balloon catheter is made of nylon, nylon elastomer, PET or PE.

The drug coated balloon catheter is configured to deliver the active drug to the target site of the blood vessels or the lumens, to treat the stenosis of the blood vessels or the lumens, and to prevent the intimal or epithelial hyperplasia; the blood vessels are the coronary artery blood vessel, the peripheral artery blood vessel or the cerebral artery blood vessel, and the lumens are the esophagus, the airway, the intestinal tract, the biliary tract, the urinary tract, the prostate, or a brain pathway.

In the drug coating on the surface of the balloon catheter of the present invention, the carriers consist of a hydrophilic substance and a hydrophilic-lipophilic substance which take synergistic effect to accelerate drug release and absorption. The hydrophilic-lipophilic substance of the carriers will be first bonded with the lipophilic drugs such as rapamycin or paclitaxel to prevent hydrophobic drug molecules from being gathered with each other or gathered on the instrument, to increase the solubility of the drug in a cell gap, and to accelerate the drugs reaching the lipid bilayer of the target tissue cell membrane. However, after the medical instrument is in contact with the tissue, the hydrophilic substance of the carriers is quickly released to promote the drugs being quickly released during positioning of the balloon catheter at a target site, thus accelerating the drug diffusion into the tissue and increasing penetration of the drugs into the tissue, the drugs are more easily absorbed by the tissue.

Compared with the prior art, the present invention has the following advantages and beneficial effects:

(1) The organic acid salt and the polyalcohol in the drug coating jointly take effect during the process of positioning the drug coated balloon catheter to promote the drugs being quickly released from the surface of the balloon and absorbed by the target tissue, and to prevent the premature release of drugs before the balloon catheter is positioned at a target site, so that the drug coated balloon catheter may generate a better drug transfer effect, and reduce drug loss during transmission.

(2) The raw materials used in the balloon catheter of the present invention may be used for intravenous injection and have better safety and biocompatibility.

DETAILED DESCRIPTION OF THE PRESENT INVENTION

Figure 1:
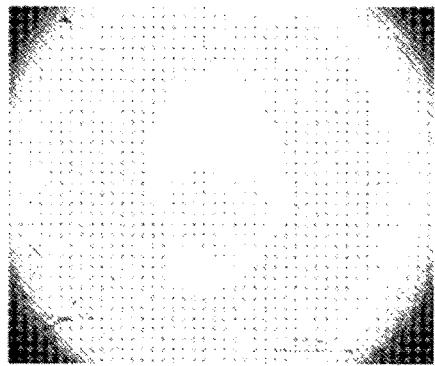
FIG. 1 is a pathological section of a vascular tissue having been dilated by a balloon catheter of in Example 3 of the present invention.

The present invention will be further described in detail with reference to the accompanying drawings and the embodiments, but the content protected by the claim of the present invention is not limited thereto.

Example 1

A coating solution was prepared by mixing 120 mg of paclitaxel, 1.0 mg of citrate, 0.1 mg of amino alcohol, 10 ml of ethanol and 4 ml of purified water, in which a mass ratio of the active drug to the carriers was 100; a PTCA balloon catheter (having a diameter of 3 mm and a length of 20 mm) with three folds was provided in a 10,000 degree clean environment, and the coating solution was dispensed on the surface of the polyester balloon by using a precision syringe (accurate to 2 μl) in a 100 degree clean environment; and then the balloon was dried, the coating solution was dispensed repeatedly until a drug concentration on the surface of the balloon reached 20 μg/mm$^2$, and the balloon was packaged and sterilized by oxirane after being dried for 24 hours.

Example 2

A solution was prepared by mixing 20 mg of rapamycin, 17 mg of lactate, 83 mg of mannitol, 7 ml of ethanol and 3 ml of purified water, in which a mass ratio of the active drug to the carriers was 0.2; a PTCA balloon catheter (having a diameter of 3 mm and a length of 20 mm) with three folds was provided in a 10,000 degree clean environment, and the coating solution was dispensed on the surface of the polyester balloon by using a precision syringe (accurate to 2 μl) in a 100 degree clean environment; and then the balloon was dried, the coating solution was dispensed repeatedly until a drug concentration on the surface of the balloon reached 1 μg/mm$^2$, and the balloon was packaged and sterilized by oxirane after being dried for 24 hours.

Example 3

A coating solution was prepared by mixing 120 mg of paclitaxel, 36 mg of sodium benzoate, 36 mg of polyethylene glycol 2000, 10 ml of ethanol and 4 ml of purified water, in which a mass ratio of the active drug to the carriers was 1.67; a PTCA balloon catheter (having a diameter of 3 mm and a length of 20 mm) with three folds was provided in a 10,000 degree clean environment, and the coating solution was sprayed on the surface of the winged polyester balloon by using a spraying equipment in a 100 degree clean environment until a drug concentration on the surface of the balloon reaches 3 μg/mm$^2$; and the balloon was packaged and sterilized by oxirane after being dried.

Example 4

A solution was prepared by mixing 100 mg of paclitaxel, 50 mg of sodium benzoate, 50 mg of polyethylene glycol 2000, 10 ml of ethanol and 4 ml of purified water, in which a mass ratio of the active drug to the carriers was 1.00; a PTCA balloon catheter (having a diameter of 3 mm and a length of 20 mm) with three folds was provided in a 10,000 degree clean environment, and the coating solution was sprayed on the surface of the winged polyester balloon by using a spraying equipment in a 100 degree clean environment until a drug concentration on the surface of the balloon reached 3 μg/mm$^2$; and the balloon was packaged and sterilized by oxirane after being dried.

Example 5

A solution was prepared by mixing 120 mg of paclitaxel, 20 mg of sodium benzoate, 20 mg of polyethylene glycol 2000, 10 ml of ethanol and 4 ml of purified water, in which a mass ratio of the active drug to the carriers was 3.00; a PTCA balloon catheter (having a diameter of 3 mm and a length of 20 mm) with three folds was provided in a 10,000 degree clean environment, and the coating solution was sprayed on the surface of the winged polyester balloon by using a spraying equipment in a 100 degree clean environment until a drug concentration on the surface of the balloon reached 3 μg/mm$^2$; and the balloon was packaged and sterilized by oxirane after being dried.

Example 6

A solution was prepared by mixing 120 mg of paclitaxel, 10 mg of sodium benzoate, 10 mg of polyethylene glycol 2000, 10 ml of ethanol and 4 ml of purified water, in which a mass ratio of the active drug to the carriers was 5.00; a PTCA balloon catheter (having a diameter of 3 mm and a length of 20 mm) with three folds was provided in a 10,000 degree clean environment, and the coating solution was sprayed on the surface of the winged polyester balloon by using a spraying equipment in a 100 degree clean environment until a drug concentration on the surface of the balloon reaches 3 μg/mm$^2$; and the balloon was packaged and sterilized by oxirane after being dried.

Comparative Example 1

A solution was prepared by mixing 50 mg of paclitaxel and 1 ml of ethanol; a PTCA balloon catheter (having a diameter of 3 mm and a length of 20 mm) with three folds was provided in a 10,000 degree clean environment, and the coating solution was sprayed on the surface of the winged polyester balloon by using a spraying equipment in a 100 degree clean environment until a drug concentration in the coating reached 3 μg/mm$^2$; and the balloon was packaged and sterilized by oxirane after being naturally dried for 24 hours.

Simulation Test for Loss in Delivery Process

Before the balloon dilatation, a simulation test of loss in the delivery process was carried out by using porcine coronary vessels to simulate target vessels of the coronary artery system; i.e., the drug loss during inserting and moving the balloon catheter to a target site.

The balloon catheters prepared from the Examples 1 to 6 and the Comparative Example 1 were respectively inserted into an in vitro simulated vascular model. In a simulated vascular system, the floating time was 90 seconds, and then the balloon catheter was taken out. Residual drug on the balloon catheter was analyzed by using HPLC, and test conditions of the HPLC were as follows: HPLC (High Performance Liquid Chromatograph) LC-20A (Shimadzu, Japan); chromatographic column: Aglilent ZOBAX SB-C18 4.6×250 mm, 5 um; flow phase:methanol to acetonitrile to water=230:360:410, column temperature of 30° C., an UV detector with a detection wavelength of 227 nm, and a flow speed of 1.0 ml/min.

HPLC test results are as shown in table 1:

Table 1 Results of the simulation test of loss in a delivery process

TABLE 1

| Number | Initial drug content (μg/mm²) | Balloon surface residual drug/initial drug % |
|---|---|---|
| Embodiment 1 | 20.0 | 57.2 |
| Embodiment 2 | 1.0 | 62.5 |
| Embodiment 3 | 3.0 | 83.0 |
| Embodiment 4 | 3.08 | 78.3 |
| Embodiment 5 | 2.81 | 80.7 |
| Embodiment 6 | 2.71 | 74.3 |
| Contrast embodiment 1 | 3.22 | 51.0 |

Table 1 results show that compared with a drug coated balloon catheter without a carrier, in the process of moving the balloon catheter of the present invention to an interventional therapy site, the loss of the drug in the vascular system was reduced, which meant that a binding power between the balloon catheter and the drug coating of the present invention was larger.

In Vitro Simulation Test

An in vitro simulation test was carried out by using porcine coronary vessels to simulate target vessels of the coronary artery system.

The PTCA balloon catheters prepared from the Examples 1 to 6 and the Comparative Example 1 were respectively inserted into simulated target vessels; the balloon was filled to about 12 atm by liquid. The over stretch ratio (i.e., a ratio of the balloon diameter to the vessel diameter) was about 1.10 to 1.20. The drug was delivered to the target tissue within a liquid filling time of 30 to 60 seconds, and then the balloon catheter was deflated and taken out from the in vitro simulation test system, and then collect the target vessel tissue. The drug content in the target tissue and the residual drug amount retained on the balloon were analyzed through tissue extraction and HPLC. Test conditions were the same as above. The results are as shown in Table 2.

Table 2 Results of the in vitro simulation test

TABLE 2

| Number | Initial drug content (μg/mm²) | Balloon surface residual drug/Initial drug % | Drug in tissue/ Initial drug % |
|---|---|---|---|
| Embodiment 1 | 20.0 | 10.2 | 2.0 |
| Embodiment 2 | 1.0 | 4.5 | 2.2 |
| Embodiment 3 | 3.0 | 2.3 | 4.2 |
| Embodiment 4 | 3.08 | 11.4 | 4.0 |

TABLE 2-continued

| Number | Initial drug content (μg/mm²) | Balloon surface residual drug/Initial drug % | Drug in tissue/ Initial drug % |
|---|---|---|---|
| Embodiment 5 | 2.81 | 14.7 | 3.9 |
| Embodiment 6 | 2.71 | 6.3 | 3.0 |
| Contrast embodiment 1 | 3.22 | 15.6 | 1.8 |

Table 2 results show that compared with the drug coated balloon catheter without a carrier, in the process of dilating the balloon catheter of the present invention, the drug absorption rate of the vascular tissue increased, and the absorption rate was related to the mass ratio of the active drug to the carrier.

Drug Release Test

The loss of the drug in the process of filling the balloon was tested.

The balloon catheters prepared from the Examples 1 to 6 and the Comparative Example 1 were filled for 2 minutes to 12 atm by liquid in PBS solution at 37° C., the residual drug on the balloon catheter was analyzed by using HPLC, and the test conditions of the HPLC were the same as above.

The results are as shown in Table 3.

Table 3 Results of the drug release test

TABLE 3

| Number | Initial drug content (μg/mm²) | Balloon surface residual drug/Initial drug % |
|---|---|---|
| Embodiment 1 | 20.0 | 39.2 |
| Embodiment 2 | 1.0 | 41.5 |
| Embodiment 3 | 3.0 | 42.0 |
| Embodiment 4 | 3.08 | 41.4 |
| Embodiment 5 | 2.81 | 44.7 |
| Embodiment 6 | 2.71 | 46.3 |
| Contrast embodiment 1 | 3.22 | 35.0 |

Table 3 results show that compared with the drug coated balloon catheter without a carrier, in the process of filling the balloon catheter of the present invention by liquid, the loss of the drug in the vascular system was reduced.

Tissue Pathological Section Test

The tissue change of the blood vessel after the balloon catheter dilatation was tested.

Figure 2:
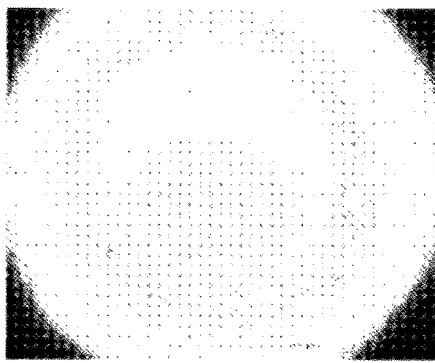
FIG. 2 is a pathological section of a vascular tissue having been dilated by a balloon catheter of Comparative Example 1.

The blood vessels on the left anterior descending coronary artery (referred to as: LAD) and the left circumflex artery (referred to as: LCX) of a miniature pig were dilated to be 1:(1.1 to 1.2) by using the balloon catheter prepared from Example 3 and the balloon catheter prepared from the Comparative Example 1 respectively; the corresponding coronary artery was taken out after 28 days, paraffin section was prepared (RM2235 paraffin slicing machine, Germany Leica Company), and the image analysis was carried out by using an optical microscope (DM2500 type microscopy measuring system, Germany Leica Company) and an image analysis software. FIG. 1 is a pathological section of the vascular tissue having been dilated by the balloon catheter of the Comparative Example 1, and FIG. 2 is a pathological section of the vascular tissue having been dilated by the balloon catheter of Example 3.

The rate of stenosis of the blood vessel having been dilated by the balloon catheter prepared from Example 3 was an average of 9.19%, and the rate of stenosis of the blood vessel having been dilated by the balloon catheter prepared from Comparative Example 1 was an average of 20.46%.

The results show that, compared with the drug coated balloon catheter without a carrier, the rate of stenosis of the blood vessel having been dilated by the balloon catheter of the present invention was obviously reduced.

The above test results show that the drug coated balloon catheter of the present invention reduces drug loss in the delivery process, and the drug in the dilating process may be relatively released to the tissue more quickly and absorbed by the tissue.

The invention claimed is:

1. A drug coated balloon catheter, comprising a balloon and a drug coating on an outer surface of the balloon, characterized in that the drug coating includes active drug/drugs and carrier/carriers, wherein the active drug is paclitaxel, and the carriers include organic acid salt and polyalcohol wherein the pacitaxel is 120 mg of paclitaxel, the organic salt is 20 mg of sodium benzoate and the polyalcohol is 20 mg of polyethylene glycol, wherein a mass ratio of the active drug to the carriers is 3.0, and a mass ratio of the organic acid salt to the polyalcohol is (0.2 to 5):1.

2. The drug coated balloon catheter according to claim 1, characterized in that a content of the active drug on the outer surface of the balloon is 3 μg/mm.

3. The drug coated balloon catheter according to claim 1, characterized in that the balloon catheter is made of nylon, nylon elastomer, PET or polyethylene.

4. A drug coated balloon catheter, comprising a balloon and a drug coating on an outer surface of the balloon, characterized in that the drug coating includes active drug/drugs and carrier/carriers, wherein the active drug is paclitaxel, and the carriers include organic acid salt and polyalcohol wherein the pacitaxel is 120 mg of paclitaxel, the organic salt is 36 mg of sodium benzoate and the polyalcohol is 36 mg of polyethylene glycol, wherein a mass ratio of the active drug to the carriers is 1.67, and a mass ratio of the organic acid salt to the polyalcohol is (0.2 to 5):1.

5. The drug coated balloon catheter according to claim 4, characterized in that a content of the active drug on the outer surface of the balloon is 3 μg/mm.

6. The drug coated balloon catheter according to claim 4, characterized in that the balloon catheter is made of nylon, nylon elastomer, PET or polyethylene.

7. A drug coated balloon catheter, comprising a balloon and a drug coating on an outer surface of the balloon, characterized in that the drug coating includes active drug/drugs and carrier/carriers, wherein the active drug is paclitaxel, and the carriers include organic acid salt and polyalcohol wherein the pacitaxel is 120 mg of paclitaxel, the organic salt is 50 mg of sodium benzoate and the polyalcohol is 50 mg of polyethylene glycol, wherein a mass ratio of the active drug to the carriers is 1.00, and a mass ratio of the organic acid salt to the polyalcohol is (0.2 to 5):1.

8. The drug coated balloon catheter according to claim 7, characterized in that a content of the active drug on the outer surface of the balloon is 3 μg/mm.

9. The drug coated balloon catheter according to claim 7, characterized in that the balloon catheter is made of nylon, nylon elastomer, PET or polyethylene.

10. A drug coated balloon catheter, comprising a balloon and a drug coating on an outer surface of the balloon, characterized in that the drug coating includes active drug/drugs and carrier/carriers, wherein the active drug is paclitaxel, and the carriers include organic acid salt and polyalcohol wherein the pacitaxel is 120 mg of paclitaxel, the organic salt is 10 mg of sodium benzoate and the polyalcohol is 10 mg of polyethylene glycol, wherein a mass ratio of the active drug to the carriers is 5, and a mass ratio of the organic acid salt to the polyalcohol is (0.2 to 5):1.

11. The drug coated balloon catheter according to claim 10, characterized in that a content of the active drug on the outer surface of the balloon is 3 μg/mm.

12. The drug coated balloon catheter according to claim 10, characterized in that the balloon catheter is made of nylon, nylon elastomer, PET or polyethylene.

* * * * *